US010302581B2

(12) United States Patent
Kjar et al.

(10) Patent No.: US 10,302,581 B2
(45) Date of Patent: *May 28, 2019

(54) REACTOR FOAM SENSOR SYSTEMS AND METHODS OF USE

(71) Applicant: Life Technologies Corporation, Carlsbad, CA (US)

(72) Inventors: Steven R. Kjar, Logan, UT (US); Jeffery O. Brown, North Logan, UT (US); Jason O. Brown, Logan, UT (US); Christopher D. Brau, Logan, UT (US)

(73) Assignee: Life Technologies Corporation, Carlsbad, CA (US)

( * ) Notice: Subject to any disclaimer, the term of this patent is extended or adjusted under 35 U.S.C. 154(b) by 213 days.

This patent is subject to a terminal disclaimer.

(21) Appl. No.: 15/430,169

(22) Filed: Feb. 10, 2017

(65) Prior Publication Data

US 2017/0152469 A1 Jun. 1, 2017

Related U.S. Application Data

(63) Continuation of application No. 14/598,881, filed on Jan. 16, 2015, now Pat. No. 9,606,077.
(Continued)

(51) Int. Cl.
*G01N 27/02* (2006.01)
*C12M 1/00* (2006.01)
(Continued)

(52) U.S. Cl.
CPC ............ *G01N 27/02* (2013.01); *C12M 21/00* (2013.01); *C12M 23/14* (2013.01); *C12M 23/26* (2013.01);
(Continued)

(58) Field of Classification Search
CPC ......... G01N 27/02; G01R 1/04; C12M 21/00; C12M 23/14; C12M 23/26; C12M 23/48;
(Continued)

(56) References Cited

U.S. PATENT DOCUMENTS 4,987,082 A * 1/1991 Gallagher .............. C12M 41/02
307/118
7,879,599 B2 2/2011 Goodwin et al.
(Continued)

FOREIGN PATENT DOCUMENTS

DE 41 42 967 A1 7/1993
DE 689 22 350 T2 1/1996
(Continued)

OTHER PUBLICATIONS

International Search Report and Written Opinion dated Apr. 28, 2015, issued in PCT Application No. PCT/US2015/011769, filed Jan. 16, 2015.

*Primary Examiner* — Michael L Hobbs

(57) ABSTRACT

A foam sensor system includes a container bounding a compartment. A foam sensor assembly is mounted on the container and includes: a base being secured to the container; a foam contact being spaced apart from the base and disposed within the compartment of the container, at least a portion of the foam contact having a first diameter; and a transition member extending between the base and the foam contact with at least a portion of the transition member being openly exposed within the compartment of the container, at least a portion of the transition member having a second diameter that is smaller than the first diameter, the foam contact and transition member being connected together so that an electrical signal can pass therethrough.

18 Claims, 7 Drawing Sheets

Related U.S. Application Data

(60) Provisional application No. 61/928,091, filed on Jan. 16, 2014.

(51) Int. Cl.
*G01R 1/04* (2006.01)
*C12Q 3/00* (2006.01)
*C12M 3/00* (2006.01)
*C12M 1/06* (2006.01)
*C12M 1/26* (2006.01)
*C12M 1/21* (2006.01)
*C12M 1/36* (2006.01)
*C12N 13/00* (2006.01)
*G01F 23/24* (2006.01)

(52) U.S. Cl.
CPC ............ *C12M 23/48* (2013.01); *C12M 27/02* (2013.01); *C12M 29/06* (2013.01); *C12M 33/04* (2013.01); *C12M 41/02* (2013.01); *C12M 41/48* (2013.01); *C12N 13/00* (2013.01); *C12Q 3/00* (2013.01); *G01F 23/24* (2013.01); *G01R 1/04* (2013.01)

(58) Field of Classification Search
CPC ...... C12M 27/02; C12M 29/06; C12M 33/04; C12M 41/02; C12Q 3/00
USPC ........................................................ 435/246
See application file for complete search history.

(56) References Cited

U.S. PATENT DOCUMENTS

| | | | |
|---|---|---|---|
| 9,606,077 B2* | 3/2017 | Kjar | G01N 27/02 |
| 2006/0196501 A1 | 9/2006 | Bibbo et al. | |
| 2009/0188211 A1* | 7/2009 | Galliher | B01F 13/0827 53/434 |
| 2011/0207170 A1 | 8/2011 | Niazi | |
| 2011/0207218 A1 | 8/2011 | Staheli et al. | |
| 2013/0082410 A1 | 4/2013 | Goodwin et al. | |

FOREIGN PATENT DOCUMENTS

| | | |
|---|---|---|
| DE | 10 2010 007 559 A1 | 8/2011 |
| EP | 0 353 830 A2 | 8/1989 |
| EP | 1 179 584 A1 | 2/2002 |
| EP | 1 950 281 A1 | 7/2008 |
| WO | 97/38088 | 10/1997 |
| WO | 2002/079374 A2 | 10/2002 |
| WO | 2011/041508 A1 | 4/2011 |

* cited by examiner

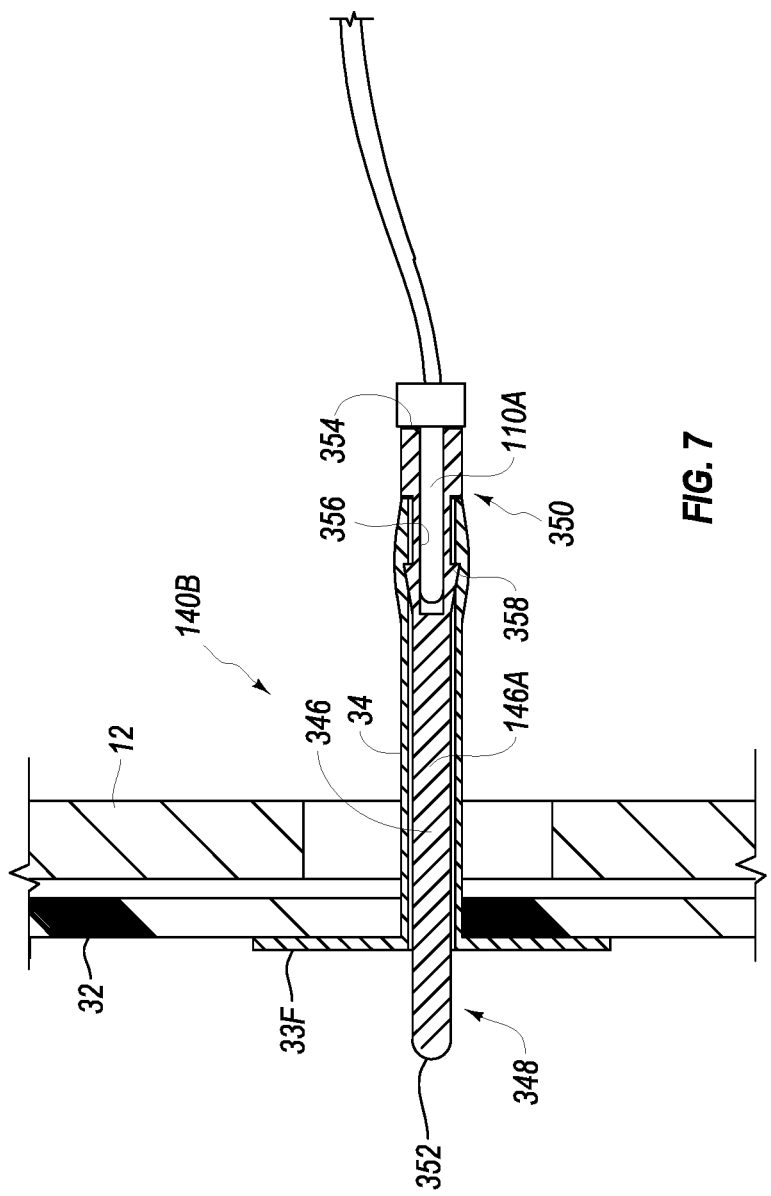

REACTOR FOAM SENSOR SYSTEMS AND METHODS OF USE

CROSS-REFERENCE TO RELATED APPLICATIONS

This application is a continuation of U.S. application Ser. No. 14/598,881, filed Jan. 16, 2015, U.S. Pat. No. 9,606,077, which claims the benefit of U.S. Provisional Application No. 61/928,091, filed Jan. 16, 2014, which are incorporated herein by specific reference.

BACKGROUND OF THE INVENTION

1. The Field of the Invention

The present invention relates to foam sensor systems used in reactors, such as bioreactors and fermenters, for controlling foam levels within the reactor bags so as to prevent unintentional clogging of the gas exhaust filters.

2. The Relevant Technology

It is now common in the biopharmaceutical industry to use bioreactors where the portion of the reactor that contacts the culture of cells is disposable so that no sterilization or cleaning is required between different batches. One example of a disposable type reactor includes a large flexible bag that is disposed within a support housing, the bag containing the cell culture that is being grown. A sparger is used to deliver needed gases to the culture while an impeller located within the bag is used to continuously mix the culture. The sparger gas exits out of the bag through a gas exhaust filter.

To help prevent or limit shear damage to the cells caused by the impeller, a surfactant is typically added to the culture. However, the combination of the surfactant, waste product from the cells, and the sparger gas passing through the culture results in the continual production of foam that collects on top of the culture within the reactor bag. If the produced foam is permitted to continue to build up within the reactor bag, the foam will eventually be drawn out of the gas exhaust line with the sparger gas and pass into the gas exhaust filter. Because the foam is very sticky, the foam will almost immediately clog the filter, thereby causing the reactor to shut down because the sparger gas can no longer escape the reactor bag. The scenario is known as "foaming-out." Once the reactor shuts down, the cells will quickly die and the entire culture will be lost. As a result, the foaming-out of a bioreactor can be extremely expensive due to the loss of the culture, the loss of the previous time and effort used in growing the culture, and the required time and expense to start the process over again with a new reactor bag and culture. In addition, foaming-out can significantly delay production time.

To help prevent foaming-out, an anti-foaming agent can be added to the culture while it is growing within the reactor bag. The effectiveness of the anti-foaming agent, however, is only temporary. As such, the bioreactor must be continually monitored through the production cycle and additional anti-foaming agent added as needed. This process, however, is labor intensive and is prone to failure if the reactor is not closely monitored. To help eliminate the required monitoring, relatively large quantities of anti-foaming agent are often added to the culture at set time intervals, independent of the foam production. This process, however, tends to use more anti-foaming agent than is actually needed to control the foam. Using anti-foaming agents and particularly excessive amounts of anti-foaming agents can be problematic in that the anti-foaming agent can build up on the surfaces that it contacts, which can cause production problems, and because the anti-foaming agent eventually needs to be removed from the culture in a downstream production step. The more anti-foaming agent in the culture, the more difficult and time consuming it is to remove the anti-foaming agent from the culture.

Accordingly, what is needed in the art are reactor systems that limit all or at least some of the above problems.

SUMMARY OF THE INVENTION

One embodiment of the present invention is directed to a foam sensor system that can include:
 a container bounding a compartment; and
 a foam sensor assembly mounted on the container and comprising:
  a base being secured to the container;
  a foam contact being spaced apart from the base and disposed within the compartment of the container, at least a portion of the foam contact having a first diameter; and
  a transition member extending between the base and the foam contact with at least a portion of the transition member being openly exposed within the compartment of the container, at least a portion of the transition member having a second diameter that is smaller than the first diameter, the foam contact and transition member being connected together so that an electrical signal can pass therethrough.

The second diameter of the transition member can be equal to or less than ⅓ of the size of the first diameter of the foam contact. Furthermore, the first diameter can be larger than 3 mm and the second diameter smaller than 1 mm.

In one embodiment, the transition member can be bent over an angle of at least 180° without plastic deformation. The transition member can be comprised of a nickel-titanium alloy or a copper-aluminum-nickel alloy.

A ground assembly can be mounted on the container and comprise a ground contact disposed within the compartment of the flexible bag. The ground assembly can be configured so that an electrical potential can be applied between the foam contact and the ground contact.

The container can comprise a flexible bag comprised of a polymeric material.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 7 is an enlarged view of an alternative embodiment of a ground assembly also shown in FIG. 1.

DETAILED DESCRIPTION OF THE PREFERRED EMBODIMENTS

Figure 1:
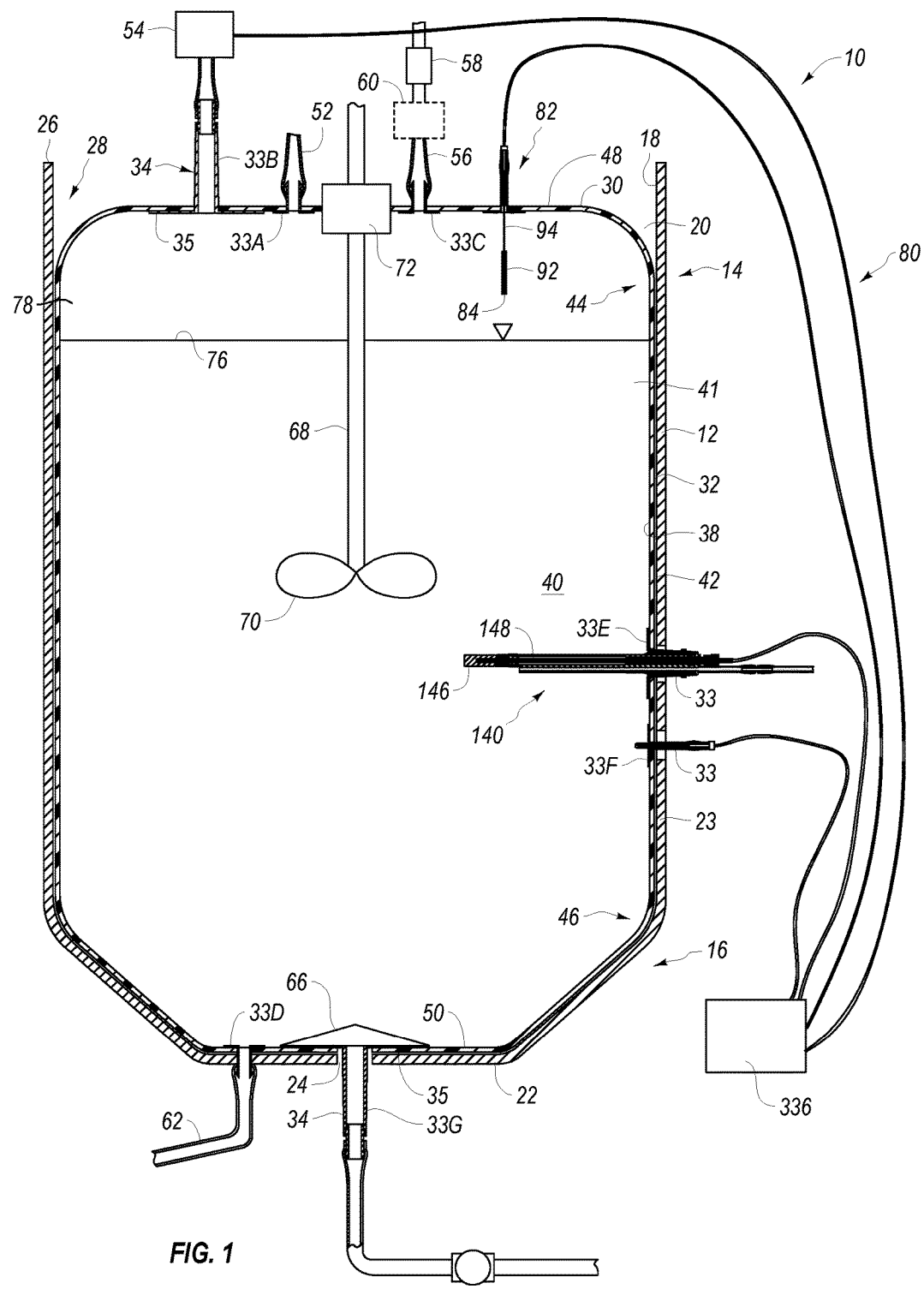
FIG. 1 is a partial cross sectional side view of a reactor system that includes a foam sensor system.

Before describing the present disclosure in detail, it is to be understood that this disclosure is not limited to particularly exemplified apparatus, systems, methods, or process parameters that may, of course, vary. It is also to be understood that the terminology used herein is only for the purpose of describing particular embodiments of the present disclosure, and is not intended to limit the scope of the invention.

All publications, patents, and patent applications cited herein, whether supra or infra, are hereby incorporated by reference in their entirety to the same extent as if each individual publication, patent, or patent application was specifically and individually indicated to be incorporated by reference.

The term "comprising" which is synonymous with "including," "containing," "having" or "characterized by," is inclusive or open-ended and does not exclude additional, unrecited elements or method steps.

It will be noted that, as used in this specification and the appended claims, the singular forms "a," "an" and "the" include plural referents unless the content clearly dictates otherwise. Thus, for example, reference to a "port" includes one, two, or more ports.

As used in the specification and appended claims, directional terms, such as "top," "bottom," "left," "right," "up," "down," "upper," "lower," "inner," "outer," "internal," "external," "interior," "exterior," "proximal," "distal" and the like are used herein solely to indicate relative directions and are not otherwise intended to limit the scope of the invention or claims.

Where possible, like numbering of elements have been used in various figures. Furthermore, alternative configurations of a particular element may each include separate letters appended to the element number. Accordingly, an appended letter can be used to designate an alternative design, structure, function, implementation, and/or embodiment of an element or feature without an appended letter. For instance, an element "80" may be embodied in an alternative configuration and designated "80a." Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element.

Various aspects of the present devices, systems, and methods may be illustrated with reference to one or more exemplary embodiments. As used herein, the term "embodiment" means "serving as an example, instance, or illustration," and should not necessarily be construed as preferred or advantageous over other embodiments disclosed herein.

Various aspects of the present devices and systems may be illustrated by describing components that are coupled, attached, and/or joined together. As used herein, the terms "coupled", "attached", "connected" and/or "joined" are used to indicate either a direct connection between two components or, where appropriate, an indirect connection to one another through intervening or intermediate components. In contrast, when a component is referred to as being "directly coupled", "directly attached", "directly connected" and/or "directly joined" to another component, there are no intervening elements present.

Unless defined otherwise, all technical and scientific terms used herein have the same meaning as commonly understood by one of ordinary skill in the art to which the present disclosure pertains. Although a number of methods and materials similar or equivalent to those described herein can be used in the practice of the present disclosure, the preferred materials and methods are described herein.

The present invention relates to foam sensors and foam sensor systems that are incorporated into a reactor system for growing cells or microorganisms or processing other fluids where foam is generated. In general, the foam sensor systems automatically and continuously detect when excessive foam is produced within a reactor so that a proper amount of an anti-foaming agent can be automatically dispensed into the reactor to prevent unwanted foam buildup. By automatically and continuously monitoring the foam level, the inventive foam sensor systems are able to maintain the produced foam within a desired level to ensure that the foam does not clog the exhaust gas filter communicating with the reactor. The systems also help to optimize the amount of anti-foaming agent used so as to avoid excessive use of anti-foaming agent.

Depicted in FIG. 1 is one embodiment of a reactor system 10 incorporating features of the present invention. Reactor system 10 can function as a bioreactor for growing cells or a fermenter for growing microorganisms. Reactor system 10 can also be used in the production of other types of fluids, such as chemicals, beverages, food products, or others, where it is desired to regulate foaming. Reactor system 10 comprises a substantially rigid support housing 12 in which a container system 30 is disposed. Support housing 12 has an upper end 14, a lower end 16, and an interior surface 18 that bounds a compartment 20. Formed at lower end 16 is a floor 22. An encircling sidewall 23 extends up from floor 22 toward upper end 14. One or more openings 24 can extend through floor 22 and sidewall 23 of support housing 12 so as to communicate with compartment 20. Upper end 14 terminates at a lip 26 that bounds an access opening 28 to compartment 20. If desired, a cover, not shown, can be hingedly or removably mounted on upper end 14 so as to cover all or part of access opening 28.

Support housing 12 can come in a variety of different sizes, shapes, and configurations. An access port can be formed on support housing 12, such as on sidewall 23 or floor 22, to permit manual access to compartment 20. The access port can be selectively closed by a door. Support housing 12 is typically made of metal, such as stainless steel, but other rigid or semi-rigid materials can also be used.

As also depicted in FIG. 1, container system 30 is at least partially disposed within compartment 20 of support housing 12 and is supported thereby. Container system 30 comprises a container 32 having a plurality of tube ports 33 mounted thereon. In the embodiment depicted, container 32 comprises a flexible bag having an interior surface 38 that bounds a chamber 40 suitable for holding a fluid 41. More specifically, container 32 comprises a sidewall 42 that, when container 32 is inflated, has a substantially circular or polygonal transverse cross section that extends between a first end 44 and an opposing second end 46. First end 44 terminates at a top end wall 48 while second end 46 terminates at a bottom end wall 50. Fluid 41 can comprise a biological culture or other foam generating fluid as discussed above.

Container 32 is comprised of a flexible, water impermeable material such as a low-density polyethylene or other polymeric sheets or films having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different material that are each separated by a contact layer. All of the layers are simultaneously co-extruded. One example of an extruded material that can be used in the present invention is the Thermo Scientific CX3-9 film available from Thermo Fisher Scientific. The Thermo Scientific CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the Thermo Scientific CX5-14 cast film also available from Thermo Fisher Scientific.

The material is approved for direct contact with living cells and is capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and US Patent Publication No. US 2003/0077466 A1, published Apr. 24, 2003 which are each hereby incorporated by specific reference.

In one embodiment, container 32 comprises a two-dimensional pillow style bag wherein two sheets of material are placed in overlapping relation and the two sheets are bounded together at their peripheries to form internal chamber 40. Alternatively, a single sheet of material can be folded over and seamed around the periphery to form internal chamber 40. In another embodiment, container 32 can be formed from a continuous tubular extrusion of polymeric material that is cut to length and the ends seamed closed.

In still other embodiments, container 32 can comprise a three-dimensional bag that not only has an annular sidewall but also a two-dimensional top end wall 48 and a two-dimensional bottom end wall 50. Three-dimensional container 32 comprises a plurality of discrete panels, typically three or more, and more commonly four or six. Each panel is substantially identical and comprises a portion of the sidewall, top end wall, and bottom end wall of container 32. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in US Patent Publication No. US 2002/0131654 A1, published Sep. 19, 2002 which is hereby incorporated by specific reference.

Container 32 is typically sterilized so that interior surface 38 and chamber 40 are sterile prior to delivering fluid 41 into chamber 40. It is appreciated that container 32 can be manufactured to have virtually any desired size, shape, and configuration. For example, container 32 can be formed having chamber 40 with a volume that is greater than, less than, or substantially equal to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although container 32 can be any shape, in one embodiment container 32 is specifically configured to be complementary or substantially complementary to compartment 20 of support housing 12. It is desirable that when container 32 is received within compartment 20, container 32 is generally uniformly supported by support housing 12. Having at least generally uniform support of container 32 by support housing 12 helps to preclude failure of container 32 by hydraulic forces applied to container 32 when filled with fluid.

Although in the above discussed embodiment container 32 is depicted and discussed as a flexible bag, in alternative embodiments it is appreciated that container 32 can comprise any form of collapsible container or semi-rigid container. Container 32 can also be transparent or opaque and can have ultraviolet light inhibitors incorporated therein.

Mounted on sidewall 42, top end wall 48, and bottom end wall 50 are a plurality of tube ports 33 which are in fluid communication with chamber 40. Each tube port 33 typically comprises a tubular stem 34 that passes through a hole on container 32 and an annular flange 35 that encircles and radially outwardly projects from stem 34. Flange 35 is welded to interior surface 38 of container 32 so as to seal closed the opening through which stem 34 passes. It is appreciated that any number of tube ports 33 can be present depending on the intended use of container 32 and that tube ports 33 can be a variety of different types, sizes and configurations. For example, tube ports 33 can be rigid or flexible and stem 34 can be formed having a substantially cylindrical configuration or formed with an outwardly encircling barb. One example of a tube port that can be used is disclosed in U.S. Pat. No. 7,879,599 which issued Feb. 1, 2011 and which is incorporated herein in its entirety by specific reference.

Each tube port 33 can serve a different purpose depending on the type of processing to be undertaken. For example, as will be discussed below in greater detail, tube port 33A is mounted on top end wall 48 and is coupled with a fluid line 52 for dispensing media, cultures, nutrients, components and/or other types of fluids and additives into chamber 40 of container 32. Tube port 33B is also mounted on top end wall 48 and is coupled with a dispenser 54 that can be activated to dispense a predetermined quantity or flow rate of anti-foaming agent into chamber 40 of container 32.

Tube port 33C is mounted on top end wall 48 and is coupled to one or more exhaust gas filters 58, either directly or through a gas exhaust line 56. Filter 58 enables gas to exit out of container 32 while preventing any contaminates from entering container 32. Filter 58 can also be used to remove any contaminates and/or moisture from the exhaust gas as it passes through filter 58. One example of a filter that can be used is a sterilizing filter that can remove contaminates down to 0.2 microns. Other filters can also be used.

More specifically, filter 58 comprises a porous material through which gas can pass but through which unwanted contaminants, such as bacteria and microorganisms, cannot. The porous material is typically hydrophobic which helps it to repel liquids. For example, filter 58 can be comprised of polyvinylidene fluoride (PVDF). Other materials can also be used. Where the system is acting as a bioreactor or fermentor, filter body 58, or the porous material thereof, typically needs to operate as a sterilizing filter and will thus typically have a pore size of 0.22 micrometers ($\mu m$) or smaller. The term "pore size" is defined as the largest pore in the material through which a particle can pass. Commonly, the porous material of filter 58 has a pore size in a range between 0.22 and 0.18 However, for pre-filtering applications or for non-sterile applications, the porous material for filter 58 can have a larger pore size, such as in a range between about 0.3 and 1.0 µm. In still other applications, the pore size can be greater than 1.0 µm. One example of filter 58 is the DURAPORE 0.22 µm hydrophobic cartridge filter produced by Millipore. Another example is the PUREFLO UE cartridge filter available from ZenPure.

If desired, a condenser 60 can be disposed between port 33C and filter 58 so that the exhaust gas passes through condenser 60. Condenser 60 can be used to remove moisture from the exhaust gas before the exhaust gas reaches filter 58. Condenser 60 thus helps to remove moisture that can clog filter 58. The condensed moisture can either be returned to container 32 or separately collected. One example of a condenser that can be used as condenser 60 and the remaining components needed to operate the condenser are disclosed in U.S. Pat. No. 8,455,242 which issued on Jun. 4, 2013 and which is incorporated herein in its entirety by specific reference. Another example of filters and condensers that can be used is disclosed in U.S. patent application Ser. No. 14/588,063, filed Dec. 31, 2014, which is incorporated herein in its entirety by specific reference. Other condensers and filters can also be used.

Tube port 33D is mounted on bottom end wall 50 and is coupled to a drain line 62. Drain line 62 can be used for sampling or otherwise dispensing fluid 41 from container 32. Tube ports 33E and 33F are also depicted as coupled with container 32 on sidewall 42 and their function will be discussed below. In addition to those depicted, other tube ports can also be mounted on container 32 for achieving other desired functions. For example, when container 32 is used as a reactor for growing cells or microorganisms, other tube ports 33 can be used to attach various probes such as temperature probes, pH probes, dissolved oxygen probes, and the like to container 32.

As also depicted in FIG. 1, a sparger 66 is mounted on container 32 for delivering controlled types and quantities of gases to fluid 41 that is disposed within container 32. This is the gas that passes out through gas filter 58. Sparger 66 can come in a variety of different sizes, shapes, and configurations and can be either secured to or freely resting on or disposed within container 32. One or more spargers can be used and, depending on their function, may emit fine bubbles of gas, larger bubbles of gas, or combinations thereof. The gas that is emitted is typically air, oxygen, nitrogen, or combinations thereof but other gases can also be used. Examples of spargers that can be used are disclosed in U.S. Pat. No. 7,384,783, issued Jun. 10, 2008, US Patent Publication No. 2006/0270036, published Nov. 30, 2006, and US Patent Publication No. 2013/0082410, published Apr. 4, 2013 which are incorporated herein in their entirety by specific reference. Other spargers can also be used.

In one embodiment it is noted that sparger 66 can be formed by securing a gas permeable sparger material to flange 35 of a tube port 33G so that by delivering a gas though stem 34, the gas is forced to travel out through the gas permeable sparger material. Further disclosure with regard to the types of materials that can be used for the gas permeable sparger material and how to attach it to flange 35 are also disclosed in the above referenced US Patent Publication No. 2006/0270036.

Although not always required, in one embodiment means are also provided for mixing fluid within chamber 40 of container 32. By way of example and not by limitation, in one embodiment a drive shaft 68 projects into chamber 40 through a dynamic seal 72 and has an impeller 70 or other mixing element mounted on the end thereof. External rotation of drive shaft 68 thus facilitates rotation of impeller 70 or other mixing element which mixes and/or suspends fluid 41 within chamber 40. Sparger 66 is typically disposed directly below the means for mixing such that the mixing or movement of the fluid produced by the mixer helps to entrain the gas bubbles within fluid 41.

In another embodiment of the means for mixing, a flexible tube can be disposed within chamber 40 having a first end coupled with container 32 by a sealed bearing and an opposing second end having an impeller or other mixing element mounted thereon. A drive shaft can be selectively passed down the tube and coupled to the impeller so that rotation of the drive shaft rotates the impeller for mixing fluid 41 but the drive shaft does not directly contact fluid 41. In another embodiment, drive shaft 65 can be configured to repeatedly raise and lower a mixing element attached thereto for mixing fluid 41. Alternatively, a magnetic stir bar can be disposed within compartment 40 of container 32 and rotated by a magnetic mixer disposed outside of container 32. In yet other embodiments, a stir bar, paddle, or the like that projects into compartment 40 of container 32 can be pivoted, swirled or otherwise moved to mix fluid 41. In addition, the mixing can be accomplished by circulating fluid through chamber 40, such as by using a peristaltic pump to move fluid 41 into and out of chamber 40 through a tube having opposing ends sealed to container 32. Gas bubbles can also be passed through the fluid to achieve the desired mixing. Finally, support housing 12 and container 32 can be pivoted, rotated or otherwise moved so as to mix the fluid within container 32. Other conventional mixing techniques can also be used.

Specific examples of how to incorporate a mixer into a flexible bag are disclosed in U.S. Pat. No. 7,384,783, issued Jun. 10, 2008; U.S. Pat. No. 7,682,067, issued Mar. 23, 2010; and US Patent Publication No. 2006/0196501, issued Sep. 7, 2006 which are incorporated herein by specific reference.

As previously mentioned, the present invention includes a foam sensor system that is used to both detect and regulate foam buildup within chamber 40 of container 32. That is, when reactor system 10 is functioning as a bioreactor or fermenter, fluid 41 comprises a culture of living cells or microorganisms. Fluid 41 has a top surface 76 disposed within chamber 40 so that a gap or head space 78 is formed between top surface 76 and top end wall 48 of container 32. To oxygenate the cells/microorganisms within fluid 41 and to otherwise regulate the chemistry within fluid 41, gas is sparged into fluid 41 through sparger 66 while the fluid within container 32 is being mixed, such as through impeller 70. A surfactant is typically added to the culture to limit unwanted shear forces on the cells or microorganisms caused by the impeller or other mixing element. The sparged gassed bubbles pass up through fluid 41 and then enter gap 78 as a humid exhaust gas. The exhaust gas passes out of gap 78 through tube port 33C and eventually exits into the environment through exhaust gas filter 58. As previously discussed, the exhaust gas can also pass through condenser 60 if needed before passing through filter 58. Because of the combination of the surfactant, the waste from the cells/microorganisms, and the sparging bubbles passing through the culture, a foam progressively begins to build up on top surface 76 of fluid 41. If the foam is left unchecked, the foam will eventually pass out through tube port 33C with the exhaust gas where it can enter and clog filter 58. Once filter 58 becomes clogged by the foam, the entire reactor system becomes inoperable and the system shuts down. As such, the culture within container 32 dies. The foam can also produce buildup and blockage within condenser 60 and can build up on other process components downstream of tube port 33C.

Figure 2:
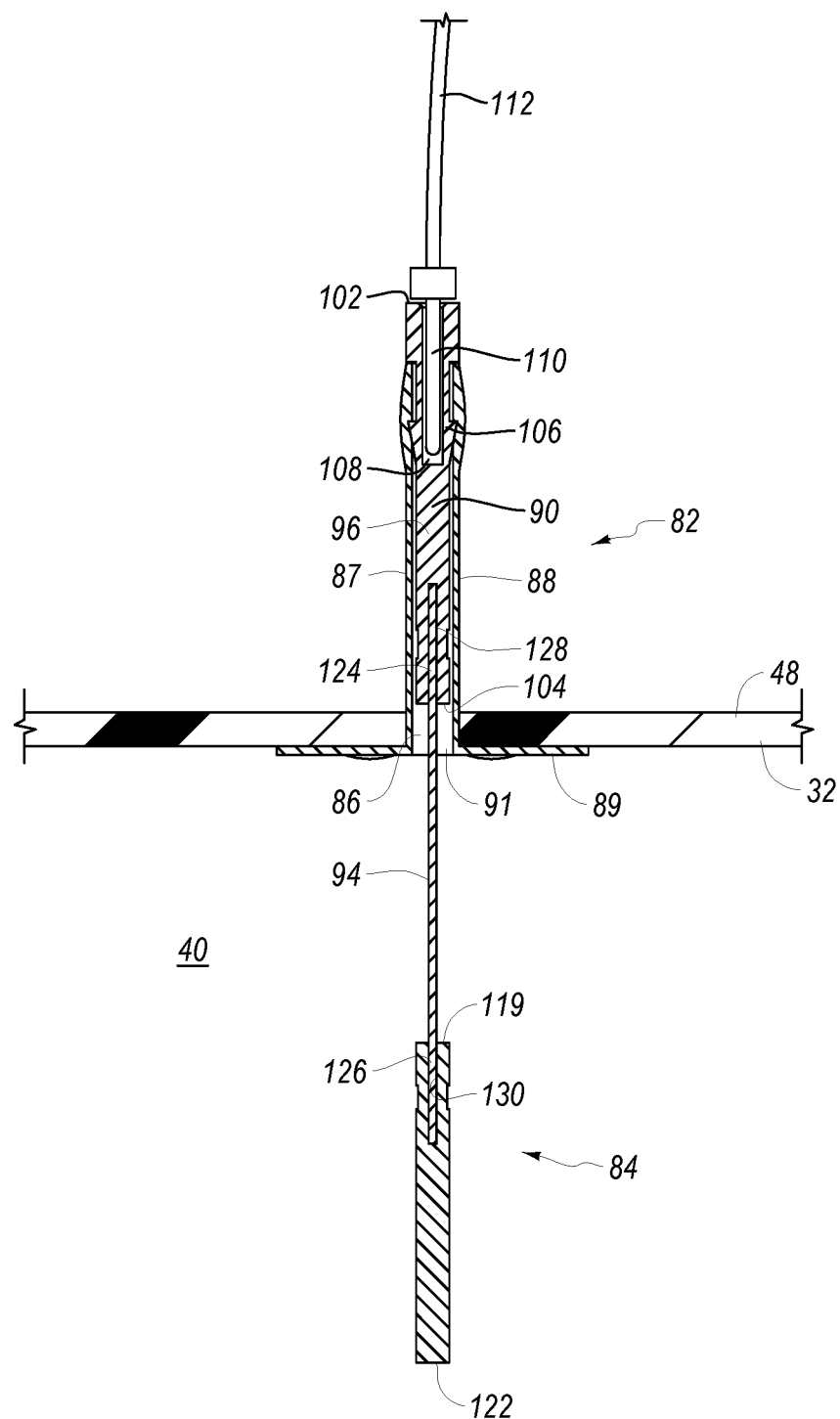
FIG. 2 is an enlarged partial cross sectional view of a foam sensor assembly shown in FIG. 1.
Figure 3:
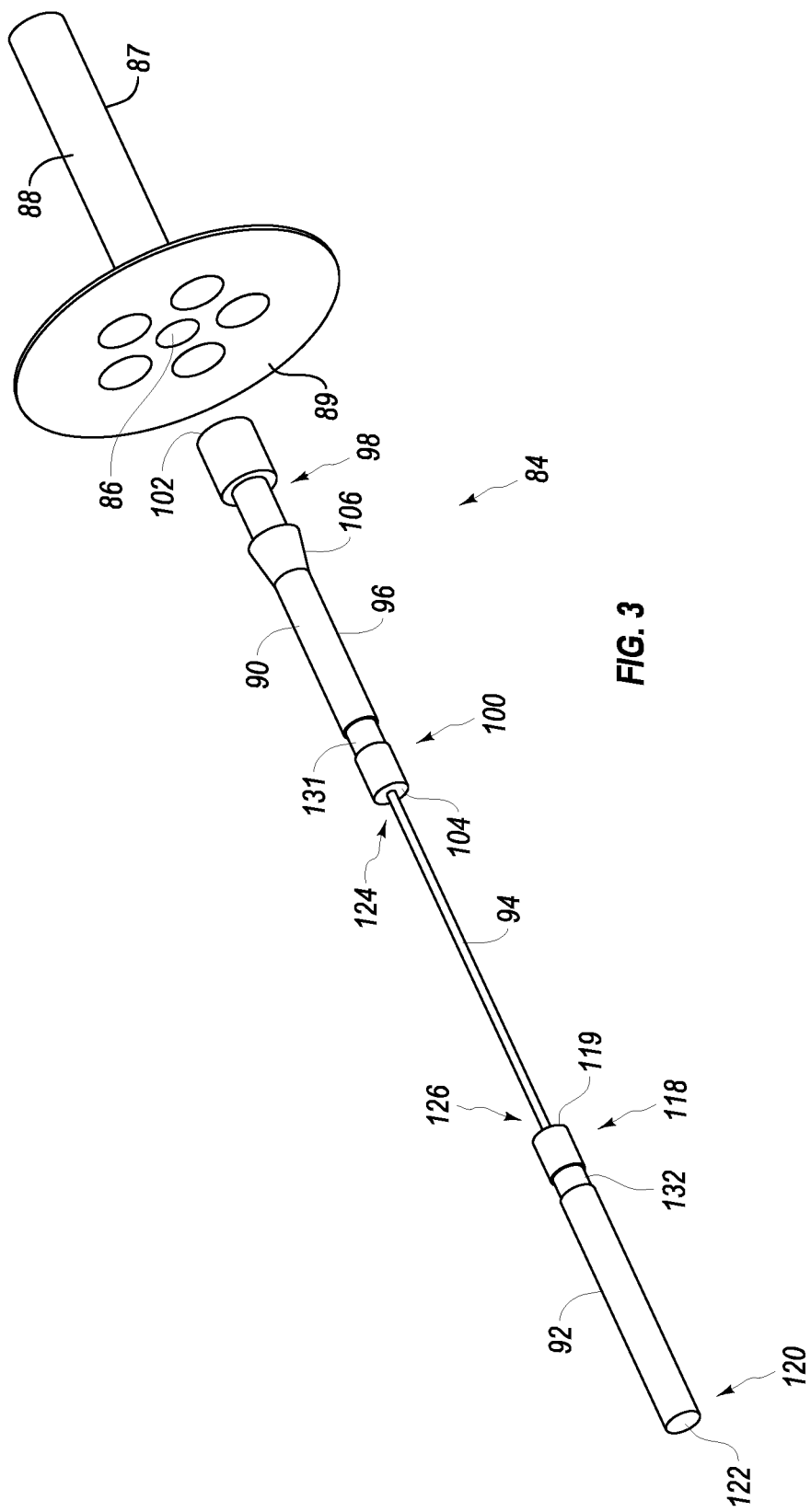
FIG. 3 is an exploded perspective view of the foam sensor assembly shown in FIG. 2.

As depicted in FIG. 1, foam sensor system 80 is provided to detect and regulate unwanted foam buildup on top surface 76 of fluid 41. Foam sensor system 80 comprises, in part, a foam sensor assembly 82 and a ground assembly 140 that are electrically connected together by a central processing unit (CPU) 336. As depicted in FIG. 2, foam sensor assembly 82 includes a housing 87 and a foam sensor 84 coupled therewith. As depicted in FIG. 3, housing 87 includes a tubular stem 88 having annular flange 89 encircling radially outwardly projecting from an end thereof. Stem 88 bounds an opening 86 that longitudinally extends therethrough. In one embodiment, housing 87 can comprise a tube port 33 and thus the designs and alternatives discussed therewith are applicable to housing 87. In other embodiments, housing 87 can be specifically designed for and manufactured with foam sensor 84. Foam sensor 84 comprises a base 90, a foam contact 92, and a transition member 94 that extends therebetween.

Base 90 comprises an elongated body 96 that is typically cylindrical and extends between a first end 98 and an opposing second end 100. First end 98 terminates at a first end face 102 while second end 100 terminates at a second end face 104. An annular barb 106 encircles and radially outwardly projects from body 96 at a location between first end 98 and second end 100. In some embodiments, barb 106 is disposed at or towards first end 98. As depicted in FIG. 2, barb 106 is sized so that when base 90 is received within opening 86 of stem 88, barb 106 outwardly pushes against the interior surface of stem 88 so as to form a liquid tight seal therebetween. As needed, a tie, crimp, or other clamp can encircle and form a constricting force on the exterior surface of stem 34 so as to enhance the seal against barb 106. Base 90 is comprised of a metal or other electrically conductive material. In one embodiment, base 90 is comprised of stainless steel. However, other metals can also be used. Furthermore, although base 90 is shown as being formed as a single integral member, base 90 can also be formed from multiple members connected together and from a plurality of stands of wires bundled, woven, or otherwise secured together, such as a cable. As needed, barb 106 can be replaced with other structure that forms a liquid tight seal with stem 88. In other embodiments, housing 87 can be over-molded onto base 90 or otherwise secured or fastened thereto so that a liquid tight seal is formed therebetween.

As also depicted in FIG. 2, a socket 108 is formed on first end face 102 so as to longitudinally project into body 96. An electrical plug 110 having electrical wiring 112 is configured to be received within socket 108 in a friction fit connection so that a positive electrical contact is made between plug 110 and base 90. In other embodiments, electrical wiring 112 can be permanently secured to body 96 such as through soldering or other electrical connections.

Returning to FIG. 3, foam contact 92 is elongated and extends between a first end 118 that terminates at a first end face 119 and an opposing second end 120 that terminates at a second end face 122. In one embodiment foam contact 92 has a length between end faces 119 and 122 in a range between 0.5 cm and 15 cm and more commonly between 1 cm and 8 cm or 2 cm and 6 cm. Other dimensions can also be used. Although not required, in the depicted embodiment, foam contact 92 has a substantially cylindrical configuration extending along the length thereof. In alternative embodiments, contact 92 can have alternative transverse cross sectional configurations such as polygonal, elliptical, irregular, or the like. Contact 92 is also made of a metal or other electrically conductive material and is typically made of stainless steel. However, other metals can also be used. Furthermore, although contact 92 is shown as being formed as a single integral member, contact 92 can also be formed from multiple members connected together and from a plurality of stands of wires bundled, woven, or otherwise secured together, such as a cable.

In contrast to base 90 and foam contact 92, which are typically made of a relatively rigid metal, in one embodiment transition member 94 can be made from a highly resiliently flexible wire that is comprised of metal or other electrically conductive material. In one embodiment, transition member 94 is made from a memory metal. Examples of memory metals include nickel-titanium alloys such as that commonly sold under the name nitinol and copper-aluminum-nickel alloys. Transition member 94 can be made from a material that enables it to be bent over an angle of at least 90° and more commonly at least 180°, 270° or at least 360° without plastic deformation. In alternative embodiments, transition member 94 can be made of a wire that bends with plastic deformation and is made of either the same or different material from base 90 or foam contact 92. In other embodiments, transition member 94 need not be a wire but can simply comprise a relatively small diameter shaft. Furthermore, although transition member 94 is shown as being formed as a single integral member, transition member 94 can also be formed from multiple members connected together and from a plurality of stands of wires bundled, woven, or otherwise secured together, such as a cable. In addition, transition member 94 can be formed as a single unity member with base 90 and/or foam contact 92. For example, base 90, transition member 94, and foam contact 92 could be molded, stamped, or cut so that they form one continuous member as opposed to two or more separate members that are secured together.

Transition member 94 is typically made of a different material than base 90 or foam contact 92. Base 90 and foam contact 92 are typically made from the same material but it is not required. In one embodiment, to attach transition member 94 to base 90 and foam contact 92, a socket 128 is formed on second end face 104 of base 90 while a socket 130 is formed on first end face 119 of foam contact 92. First end 124 of transition member 94 is received within socket 128 while second end 126 of transition member 94 is received within socket 130. A crimp force can then be applied around a portion of base 90 and foam contact 92 encircling transition member 94 so that the opposing ends of transition member 94 are held by crimp connection within base 90 and foam contact 92. The crimping force can produce a recessed crimp groove 131 on base 90 and a crimp groove 132 on foam contact 92. Other methods of attachment can also be used. In one embodiment the exposed portion of transition member 94 has a length in a range between 2 cm and 15 cm and more commonly between 3 cm and 10 cm or 4 cm and 8 cm. Other dimensions can also be used.

Foam sensor assembly 82 is typically assembled as depicted in FIG. 2. That is, base 90 is received within stem 88 so as to form a liquid tight seal therewith. Second end face 104 of base 92 is also typically disposed within opening 86 of stem 88 so that at least a portion of first end 124 of transition member 94 is disposed within opening 86 while second end 126 of transition member 94 is disposed within compartment 40 of container 32. Foam contact 92 is disposed completely within compartment 40 of container 32 and is typically located so that end face 122 is at a distance between 3 cm and about 25 cm from top end wall 48 of container 32 during operation of reactor system 10 and is more commonly between 5 cm and 15 cm or 6 cm and 12 cm from top end wall 48. Other distances can also be used depending on the application. In an alternative embodiment, foam sensor assembly 82 can be mounted on sidewall 42 of container 32 at first end 44. Again, however, in this embodiment end face 122 is also typically located within the above ranges from top end wall 48 of container 32 during operation of reactor system 10. In both embodiments, the pressure of the gas within compartment 40 supports container 32 in an inflated position and concurrently supports foam sensor assembly 82.

By making transition member 94 out of a resiliently flexible wire, container system 30 can be folded or rolled up for storage, transport, and/or sterilization even after foam sensor 84 has been attached without risk of damage to foam sensor 84 or to container 32. That is, transition member 94 bends when container system 30 is folded or rolled up so that foam sensor 84 does not break or puncture container 32. When container 32 is unfolded and inflated, transition member 94 resiliently returns to its original desired configuration. Transition member 94 is also shown as having a smaller diameter than foam contact 92. The benefits derived from having this difference in diameter will be discussed later below.

Figure 4:
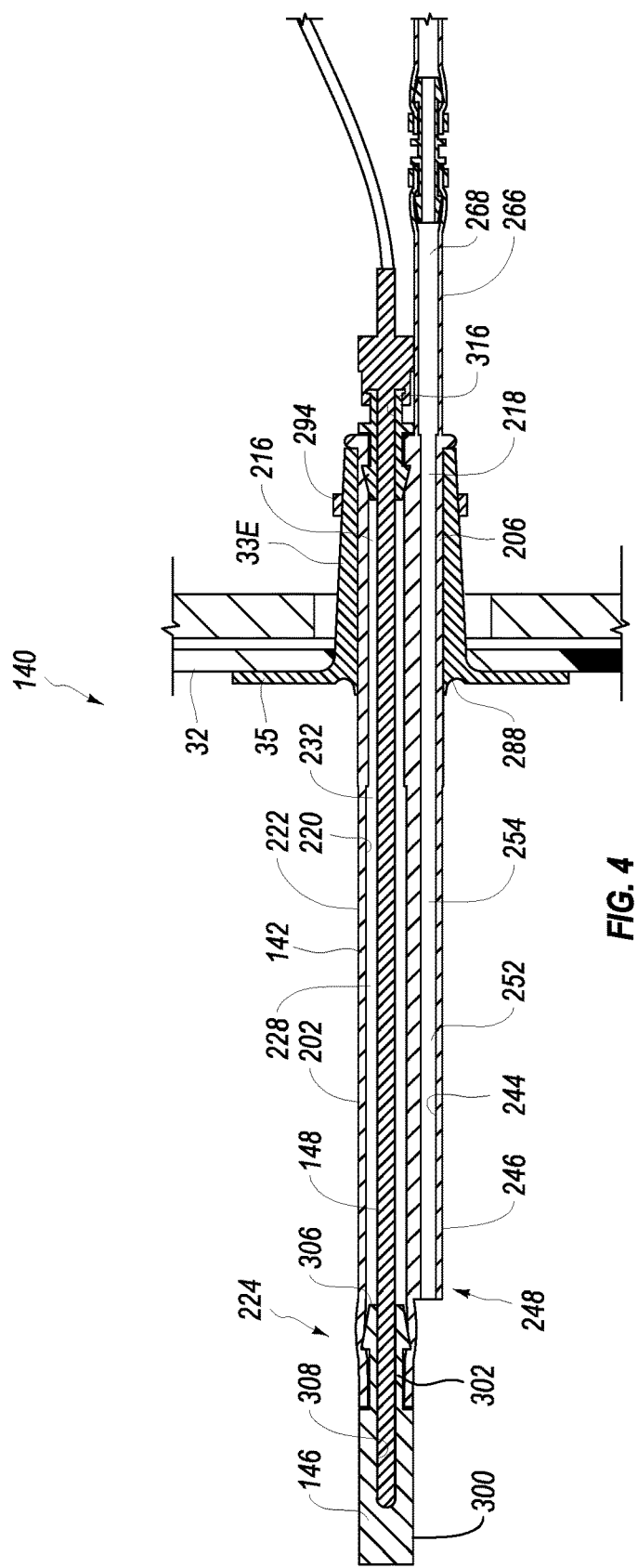
FIG. 4 is an enlarged cross sectional side view of one ground assembly shown in FIG. 1.

Foam sensor system 80 also includes ground assembly 140 that acts in conjunction with foam sensor assembly 82. Depicted in FIG. 4 is one embodiment of ground assembly 140 that has multiple uses. In general, ground assembly 140 comprises a tube assembly 142 (which can also be referred to herein as a housing), a tube port 33E that couples tube assembly 142 to container 32, a ground contact 146 coupled to an end of tube assembly 142, and a probe 148 that is received within tube assembly 142 and engages with ground contact 146. A more detailed description of the elements of ground assembly 140 will now be provided.

Figure 5:
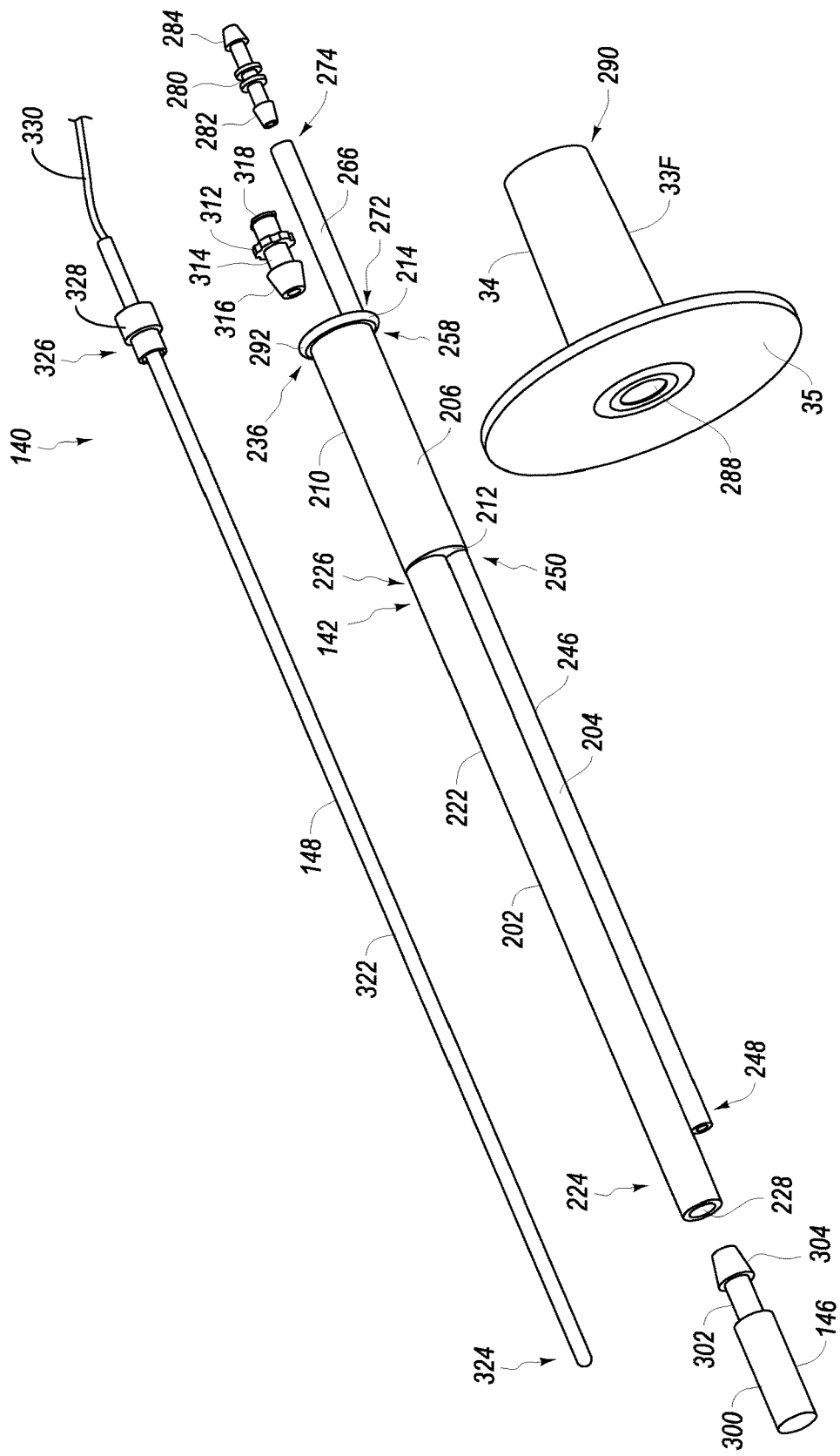
FIG. 5 is an exploded perspective view of the ground assembly shown in FIG. 4.

As depicted in FIGS. 4 and 5, tube assembly 142 comprises an elongated flexible probe tube 202 and an elongated flexible sampling tube 204 each coupled to a body 206. Body 206 of tube assembly 142 has a generally cylindrical shape with an exterior surface 210 extending between a first end face 212 and an opposing second end face 214. Body 206 bounds a first passage 216 and a second passage 218 each extending between first end face 212 and second end face 214. In one embodiment, first passage 216 and second passage 218 extend in adjacent parallel alignment with each other substantially the full length of body 206. In alternative embodiments, exterior surface 210 of body 206 can have a variety of alternative transverse cross sections such as elliptical or polygonal, or irregular.

Probe tube 202 of tube assembly 142 has an interior surface 220 and an opposing exterior surface 222 each extending between a first end 224 and a longitudinally spaced apart second end 226. Interior surface 220 bounds a first passageway 228 that longitudinally extends through probe tube 202. As discussed below in greater detail, ground contact 146 couples with first end 224 of probe tube 202. Second end 226 of probe tube 202 is coupled with first end face 212 of body 206 so as to communicate with first passage 216 of body 206. In this manner, first passageway 228 of probe tube 202 and first passage 216 of body 206 combine to form a probe passage 232 having a first end 224 and a second end 236 at or toward second end face 214 of body 206.

Similar to probe tube 202, sampling tube 204 of tube assembly 142 has an interior surface 244 and an opposing exterior surface 246 each extending between a first end 248 and a longitudinally spaced apart second end 250. Interior surface 244 bounds a second passageway 252 that longitudinally extends through sampling tube 204. Second passageway 252 is open at first end 248 and second end 250, thus allowing fluid communication completely through sampling tube 204. Second end 250 of sampling tube 204 is coupled with first end face 212 of body 206 so as to communicate with second passage 218 of body 206. In this manner, second passageway 252 of sampling tube 204 and second passage 218 of body 206 combine to form a sampling passage 254 having a first end 248 and a second end 258 at or toward second end face 214 of body 206, allowing fluid communication therethrough.

At least a portion of sampling tube 204 extends along probe tube 202 in adjacent parallel alignment with first end 248 of sampling tube 204 being disposed at or toward first end 224 of probe tube 202. In the embodiment depicted, sampling tube 204 is in adjacent parallel alignment with probe tube 202 along the entire length of sampling tube 204. To facilitate the parallel alignment, sampling tube 204 is coupled with probe tube 202 along the entire length of sampling tube 204 such as by being integrally molded together or secured together such as by an adhesive or other fasteners. In alternative embodiments, sampling tube 204 can be coupled to probe tube 202 at spaced apart locations. As a result of this coupling, when probe 148 is inserted into probe tube 202, as described below, sampling tube 204 also becomes substantially rigid as it extends into chamber 40 of container 32.

In the embodiment depicted, sampling tube 204 is of a smaller diameter than probe tube 202. It is appreciated that in alternative embodiments, sampling tube 204 can have a larger diameter than or have the same diameter as probe tube 202. Sampling tube 204 and probe tube 202 each have a length in a range typically between about 2 cm to about 40 cm with about 5 cm to about 25 cm being more common. Other lengths can also be used.

Probe tube 202, sampling tube 204, and body 206 can be molded as a unitary integral piece. Alternatively, probe tube 202 and sampling tube 204 can be connected to each other and/or to body 206 by welding using conventional welding techniques such as heat welding, RF energy, ultrasonic, and the like or by using adhesives other any other conventional attaching or fastening techniques.

In some embodiments, an elongated collection tube 266 bounding a third passageway 268 extends outward from second end face 214 of body 206. Collection tube 266 has a first end 272 coupled with second end face 214 of body 206 so as to communicate with sampling passage 254 and has an opposing second end 274. A tubular coupler 280 has a first end 282 with an annular barb formed thereon that can be received within second end 274 of third passageway 268 to form a liquid tight connection therewith. Tubular coupler 280 has a second end 284 with an annular barb formed thereon that can be received within a separate fluid line for delivering fluid collected from sampling tube 204 to a desired location, such as a collection bag or other container. Alternatively, collection tube 266 can be used to retrieve fluid or other material from a container to insert the fluid into chamber 40.

In one embodiment, tube assembly 142 is molded from a soft, resiliently flexible polymeric material or elastomeric material such as polyethylene, silicone or KRATON® having a durometer on a Shore A scale with a value of less than 90 and more preferably less than 70 but typically greater than 5. In other embodiments, other thermoset or thermoplastic polymers having a durometer in the above range can also be used. Other materials such as those previously discussed with regard to container 32 can also be used. In some embodiments, as a result of the material properties, probe tube 202 and sampling tube 204 can be manually folded over so as to kink the passages therein closed or probe tube 202 and sampling tube 204 can be manually pinched, such as by a clamp, to close the passages therein without permanent deformation to probe tube 202 or sampling tube 204.

Continuing with FIGS. 4 and 5, tube port 33E includes stem 34 and annular flange 35 as previously discussed. In this embodiment, an annular lip seal 288 radially inwardly projects from the interior surface of stem 34 at or toward the end from which flange 35 projects. Tube port 33E and the other tube ports disclosed herein can be made of the same materials as discussed above with regard to tube assembly 142. Further disclosure and alternative embodiments for tube port 33F are set forth in U.S. Pat. No. 7,879,599, issued Feb. 1, 2011 which is incorporated herein in its entirety by specific reference. Body 206 of tube assembly 142 has a substantially cylindrical configuration that is configured to snugly fit within stem 34 of tube port 33F so that a liquid tight seal is formed therebetween.

During assembly, flange 35 is welded to the interior surface of container 32 so that stem 34 outwardly projects through an opening thereon. Probe tube 202 and sampling tube 204 of tube assembly 142 are advanced through stem 34 of tube port 33E. Tube port 33 is advanced over body 206 until end 290 of stem 34 butts against an annular shoulder 292 outwardly projecting from the second end of body 206. As depicted in FIG. 4, in this position lip seal 288 radially biases against the exterior surface of body 206 at the first end thereof so as to form a sealed engagement therebetween. To provide a more secure engagement and seal between stem 34 and body 206, one or more pull ties, clamps, or other tightening devices can be used. For example, in the embodiment depicted a plastic pull tie 294 is secured around a portion of tubular stem 34 disposed over body 206 so as to further secure the sealed engagement therebetween. In an alternative method of assembly, flange 34 can be welded to container 32 after tube assembly 142 is secured to tube port 33E.

As also depicted in FIGS. 4 and 5, ground contact 146 comprises a cylindrical body 300 having a stem 302 projecting from an end thereof and an annular barb 304 encircling and radially outwardly projecting from stem 302. Stem 302 terminates at an end face 306 into which a blind socket 308 is formed. Ground contact 146 is formed from a metal such as stainless steel or other electrically conductive materials. During assembly, stem 302 is received within first end 224 of probe tube 202 so that annular barb 304 forms a liquid tight seal between ground contact 146 and probe tube 202. In the assembled configuration, blind socket 308 is aligned and in communication with probe passage 232 of probe tube 202.

A fitting 312 is secured to tube assembly 142 so as to be in communication with the second end of the probe passage 232. Fitting 312 comprises a tubular stem 314 that has an interior surface bounding a passageway 316 extending therethrough. Stem 314 has a first end with an annular barb 316 encircling and radially outwardly projecting therefrom and an opposing second end with a lure lock thread 318 or other connector formed thereon. During assembly, the first end of stem 314 is received within the second end of probe passage 232 so that barb 316 forms a secured engagement with tube assembly 142.

As previously mentioned, ground assembly 140 also includes probe 148. Probe 148 comprises an elongated probe stem 322 having a first end 324 and an opposing second end 326. The connector 328 encircles and is mounted on second end 326 of probe stem 322. In this embodiment, connector 328 comprises a female lure lock. However, other types of connectors that mate with fitting 312 can also be used. Electrical wiring 330 is attached to and communicates with probe stem 322 at second end 326. Probe stem 322 is comprised of a metal or other electrically conductive material so that an electrical charge or signal can pass along the length of probe stem 322 and into electrical wiring 320. In one embodiment, probe 148 is also configured to function as a temperature sensor probe, such as a resistance temperature detector (RTD).

During assembly, first end 324 of probe stem 322 is advanced through fitting 312 along probe passage 232 and into blind socket 308 of ground contact 146. Probe stem 322 has a close tolerance fit within blind socket 308 so that an electrical signal or current can be passed between ground contact 146 and probe 148. To help facilitate a positive engagement between probe 148 and ground contact 146, probe stem 148 has a length slightly longer than the combined length of probe passage 232 and blind socket 308. As a result, to enable connector 328 to engage with fitting 312, probe 148, in one embodiment, must be pushed into probe passage 232 so that tube assembly 142 stretches a distance before connector 328 reaches and can be secured to fitting 312. This assembly results in a positive biasing force between first end 324 of probe 148 and ground connector 146 so as to help ensure a good electrical contact therebetween. Other electrical connections can also be used. An additional benefit of securing probe 148 within probe passage 232 as discussed above is that it forces sampling tube 204 to project into container 32 so that sampling fluid can be taken at a location away from the wall of container 32.

Because probe tube 202 is sealed closed at first end 224 by ground contact 146, probe 148 or other support inserted into probe tube 202 does not directly contact the liquid or other material within chamber 40 of container 32. As a result, probe 148 can be inserted and extracted from probe passage 232 without fear of any liquid or other material leaking out of chamber 40 or becoming contaminated by probe 148. Furthermore, because probe 148 does not contact the contents of chamber 40, probe 148 can be repeatedly used without the need for sterilization or cleaning between uses.

In the fully assembled configuration as depicted in FIG. 1, both probe 148 of ground sensor 140 and foam sensor 84 are in electrical communication with central processing unit (CPU) 336. CPU 336 applies an electrical potential or voltage between probe 148 (and thus also ground contact 146) and foam sensor 84. As previously discussed, during the operation of reactor system 10, foam slowly starts to build on top surface 76 of fluid 41. Once foam builds up sufficiently high on top surface 76 so as to contact foam contact 92 of foam sensor 84, an electrical signal is passed between foam sensor 84 and ground contact 146/probe 148 by passing through the foam and through fluid 41.

The electrical signal is sensed by CPU 336 which in turn signals dispenser 54 to dispense a predetermined quantity of anti-foaming agent into container 32 which temporarily dissipates or at least diminishes the foam buildup. CPU 336 can be programed in a variety of different ways to dispense the anti-foaming agent. For example, the anti-foaming agent can be dispensed as a large bolus after which CPU 336 waits for a period before checking again for an electrical signal. Alternatively, the anti-foaming agent can be slowly and continuously released once the signal is detected and then stopped once CPU 336 can no longer detect the electrical signal. Other methods can also be used. By automatically and continually monitoring the foam level using foam sensor system 80, the foam level can be maintained sufficiently low that there is no risk of the foam passing out of gas exhaust port 33C and clogging gas filter 58. In addition, foam sensor system 80 only dispenses the amount of anti-foaming agent needed to maintain the foam within the desired level. As such, less anti-foaming agent is added to the culture and thus less anti-foaming agent needs to be removed from the culture.

One of the challenges of foam sensor system 80 is that the foam is relatively sticky and adheres to both the interior surface of container 32 and to foam sensor 84. As a result of the gas flowing through gap 78 and the humid vapor within gap 78 that can carry small particles of foam, a thin layer of foam can build up on interior surface 38 of container 32 within gap 78 and on the exposed portion of foam sensor 84 within gap 78. In addition, the foam does not generally build up as an even layer on top surface 76 of fluid 41 but typically builds up in clumps. The clumps may obtain a height that extends up to transition member 94 (FIG. 2) before the foam first encounters foam sensor 84. These clumps can also help build up a layer of foam on the interior surface of container 32 within gap 78 and on the exposed portion of foam sensor 84 within gap 78. If a continuous layer of foam is formed on interior surface 38 of container 32 from the top surface 76 of fluid 41 to foam sensor 84, an electrical signal ("false signal") can pass between foam sensor 84 and ground contact 146 by passing through the foam layer on container 32 and fluid 41. This false signal will give a false reading to CPU 336 that the foam layer on fluid 41 has reached foam contact 92 and thus trigger the dispensing of anti-foaming agent into fluid 41 when no anti-foaming agent may be needed. Furthermore, because of the foam layer on container 32, the false reading may continue even after the anti-foaming agent is added, thereby resulting in continued or repeated unwanted dispensing of anti-foaming agent into fluid 41.

Foam sensor 84 is specifically designed with transition member 94 having a smaller diameter than foam contact 92 to help differentiate between a true signal where the signal is produced as a result of foam building up on top surface 76 of fluid 41 so as to contact foam contact 92 and a false signal where the signal is produced as a result of a thin film of foam coating the interior surface of container 32 so as to extend between foam sensor 84 and fluid 41. Specifically, electrical conductance is in part related to the surface area of an electrical contact and the volume of the material through which the electrical current passes. Accordingly, the electrical current of the true signal will always be greater than the electrical current of the false signal. This is true because the volume of foam through which the true electrical signal passes between foam sensor 84 and fluid 41 is larger than the volume of foam through which the false electrical signal passes on interior surface 38 of container 32 between foam sensor 84 and fluid 41. Furthermore, because foam contact 92 has a larger diameter than transition member 94, foam contact 92 will have more surface area contacting the foam on top of fluid 41 than transition member 94 will have contacting the thin film of foam on the surface of container 32.

Accordingly, CPU 336 can be programmed so that when the electrical signal from foam sensor system 80 is below a predetermined value it is assumed to be a false signal and no anti-foaming agent is released but when the signal exceeds the predetermined value, it is assumed to be a true signal and the anti-foaming agent is released as discussed above. The predetermined value on which to determine a true or false signal can be the measured electrical signal strength or conductivity. For example, in one embodiment, only signals having a conductivity of greater than 20µ Siemens and more commonly greater than 30µ Siemens or 40µ Siemens will be determined to be a true signal. It is appreciated that the predetermined conductivity value can be set over a wide range depending on factors such as the amount of voltage applied between foam contact 92 and foam ground 146, the relative diameters between transition member 94 and foam contact 92, the materials used for the contacts and other factors. In other embodiments, the predetermined value can be set at any value between 20µ Siemens and 50µ Siemens. Other values can also be used. Likewise, other measurements, such as current, can also be used as the predetermined value.

To help differentiate between the true signal and the false signal, foam contact 92 will typically have a diameter normal to the longitudinal length thereof that is at least 3, 4, 5, 6, 8, or 10 times larger than a diameter of transition member 94 disposed within chamber 40 of container 32 as measured normal to the longitudinal length thereof. Expressed in other terms, a diameter of transition member 94 can be at most ⅓, ¼, ⅕, ⅙, ⅛, or 1/10 of a diameter of foam contact 92. Because diameters can change along the length of foam contact 92 and transition member 94, the above measured and compared diameters for foam contact 92 and transition member 94 can be selected as a maximum diameter, minimum diameter, average diameter over the length thereof or a diameter at any location on or over at least a portion of foam contact 92 and transition member 94. Other ratios can also be used. The diameter of foam contact 92 is typically greater than 2 mm, 3 mm, 5 mm, 7 mm or 10 mm or in a range between 2 mm an 10 mm while the diameter of transition member 94 is typically less than 2.5 mm, 2 mm, 1.5 mm, 1 mm, 0.75 mm or 0.5 mm or in a range between 2.5 mm and 0.5 mm. Again, these diameters can be a maximum diameter, minimum diameter, average diameter over the length or a diameter at any location on or over at least a portion of foam contact 92 or transition member 94. Other dimensions can also be used. It is noted that the term "diameter" as used herein refers to a straight line or the length of such line passing from side to side of the corresponding structure, through its center, and is not intended to limit the structure to a circular or any other defined shape. As the diameter of transition member 94 continues to increase above 2 mm, the ability to differentiate between the true and false signal decreases. Likewise, as the diameter of transition member 94 decreases, particularly below 0.5 mm, the risk of structural failure of transition member increases.

As depicted in FIG. 2, in the assembled state a cavity 91 (comprising a portion of opening 86) is formed in stem 88 extending from flange 89 to second end face 104 of base 90. Transition member 94 centrally extends through cavity 91 with an annular gap formed between transition member 94 and the encircling interior surface of stem 88. Because the system is pressurized as a result of the inflow of sparging gas, foam will typically not enter or build up within cavity 91. However, foam can bridge between transition member 94 and tubular stem 88 or flange 89 at the opening to cavity 91. The bridging typically occurs as a result of a clump of foam contacting and adhering to transition member 94, as a result of foam colleting within compartment 40 of container 32, and remaining on transition member 94 even when the remainder of the foam is dissipated as a result of the addition of an anti-foaming agent. The false signal can be produced as a result of the foam bridge contacting the foam build-up on interior surface 38 of container 32, thereby completing the circuit to ground contact 146, as discussed above.

To help eliminate or minimize the formation of a foam bridge between transition member 94 and tubular stem 88/flange 89 (and thereby minimize any false signal), the diameter of opening 86/cavity 91 within housing 87 can be increased relative to the diameter of transition member 94. For example, while the diameter of transition member 94 is typically in the values as discussed above, the inside diameter of opening 86/cavity 91 encircling transition member 94 is typically greater than 5 mm, 10 mm, 15 mm, 20 mm, 30 mm, 40 mm or 50 mm. Other dimensions can also used. In general, the larger the diameter, the lower the probability that a foam bridge can be formed and maintained between transition member 94 and tubular stem 88/flange 89. Other dimensions can also used. It is also noted that cavity 91 typically has a depth extending between flange 89 to second end face 104 of base 90 that is in a range between 5 mm and 50 mm with between 10 mm to 30 mm or 10 mm to 20 mm being more common. Other dimensions can also be used.

As previously mentioned, in some embodiments foam sensor 82 can be disposed on sidewall 42 (FIG. 1) of container 32 so as to be positioned within head space 78. In this embodiment, it is typically preferred that housing 87 be angled downward relative to the horizontal so that condensate that forms within cavity 91 freely flows out of cavity 91 and into chamber 40 of container 32. This configuration helps to prevent the condensate from collecting in cavity 91 which could assist in the formation of a false signal, as discussed above. In one embodiment, housing 87 can be positioned so that a longitudinal axis centrally extending through opening 86 or cavity 91 of housing 87 is disposed at a downward angle relative to the horizontal in a range between about 10° to about 70° with between about 30° to about 45° being more common. Other angles can also be used.

In other embodiments, it is also envisioned that foam sensor 84 could be formed where transition member 94 is eliminated. For example, foam contact 92 could extend all the way to body 96 and have a constant diameter along the length thereof by applying a coating or insulative material over the center of the foam contact which will not permit the foam to stick thereto. As such, no false signals would be produced.

Figure 6:
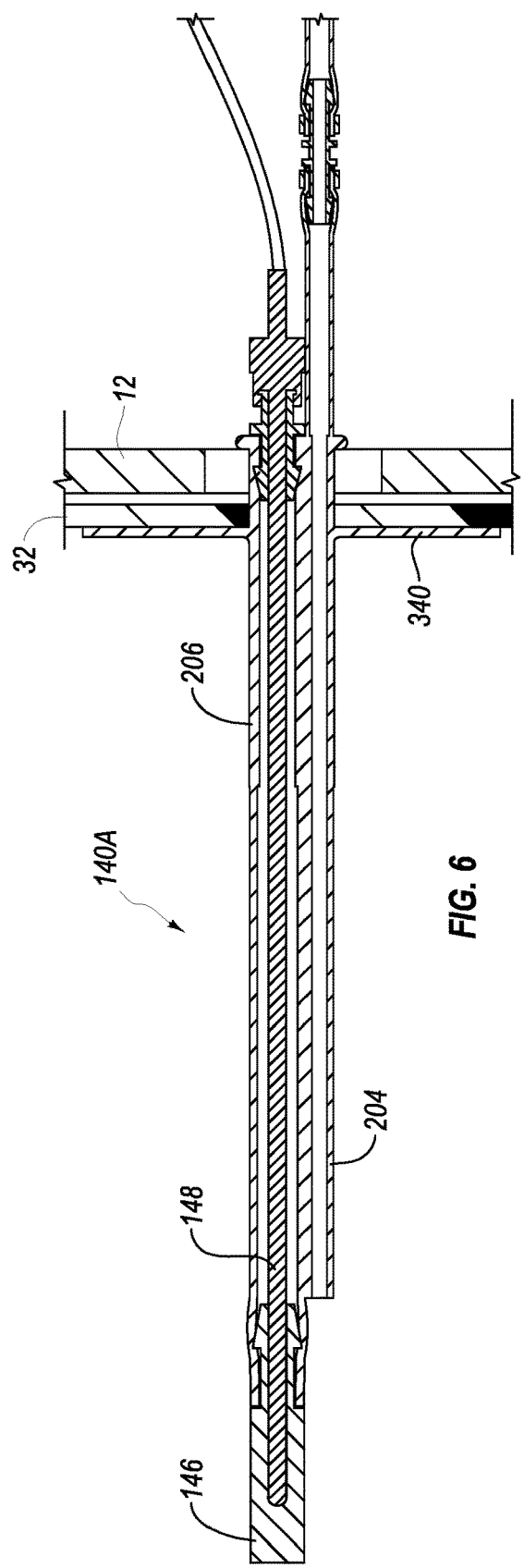
FIG. 6 is a cross sectional side view of an alternative embodiment of the ground assembly shown in FIG. 4.

It is appreciated that ground assembly 140 can have a variety of different configurations. For example, depicted in FIG. 6 is one embodiment of a ground assembly 140A wherein like elements between ground assembly 140 and 140A are identified by like reference characters. The only difference between ground assembly 140A and 140 is that in ground assembly 140A, tube port 33E has been eliminated. In this embodiment, an annular flange 340 encircles and radially outwardly projects from body 206 and is integrally molded or otherwise formed therewith. Flange 340 is welded directly to the interior surface of container 32. In other embodiments, it is appreciated that sampling tube 204 can be eliminated from the ground assembly and that probe 148 need not be designed to function as a temperature sensor. That is, probe 148 can be limited to functioning only to conduct the signal that passes to or from foam sensor 84. Examples of other embodiments of tube assemblies 142 that can be modified to operate with ground contact 146 are disclosed in U.S. Pat. No. 7,879,599 which was previously incorporated herein by specific reference.

Depicted in FIG. 7 is an alternative embodiment of a ground assembly 140B that can be used in place of ground assembly 140 or 140A. Ground assembly 140B comprises port 33F as previously discussed (and which can also be referred to herein as a housing) and a ground contact 146A. Ground contact 146A comprises an elongated body 346 that extends between a first end 348 and an opposing second end 350. First end 348 terminates at a rounded nose 352 while second end terminates at an end face 354. A blind socket 356 is formed on end face 354 and is configured to receive an electrical plug 110A. An annular barb 358 encircles and radially outwardly projects from body 346 at or towards second end 350. Ground contact 146A is manually inserted within stem 34 of port 33F so that barb 358 forms a fluid tight seal with stem 34 while nose 352 projects into container 32. Again, an electrical potential or voltage is applied between ground assembly 140B and foam sensor assembly 82 so that an electrical signal is passed therebetween when foam reaches foam contact 92. In other embodiments, port 33F can couple with ground contact 146A in the same way that housing 87 couples with base 90 as discussed above with regard to foam sensor 84. Other designs for a ground assembly can also be used.

In view of the forgoing, embodiments of the inventive foam sensor system provide a number of advantages. Notably, select embodiments provide an automated mechanism for determining when an anti-foaming agent should be dispersed into container 32 so as to control the foam level within container 32 and thereby avoid the risk that the gas filter will become clogged. By using the automated system, less monitoring of the reactor is required. Furthermore, the amount of anti-foaming agent that is used is minimized, thereby limiting the problems associated with anti-foaming agents and requiring less anti-foaming agent to be removed from the culture. Select embodiments are also designed to enable easy collapsing and folding of container 32 for shipping, transport, sterilization or the like with minimal risk of damage to the foam sensor assembly or container 32. Select embodiments also provide a mechanism to help eliminate any false readings that could be produced as a result of foam coating the interior surface of container 32 and contacting a portion of the foam sensor assembly. Other advantages are also achieved.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A foam sensor system comprising:
   a container bounding a compartment; and
   a foam sensor assembly mounted on the container and comprising:
   a base being secured to the container;
   a foam contact being spaced apart from the base and disposed within the compartment of the container, at least a portion of the foam contact having a first diameter; and
   a transition member extending between the base and the foam contact with at least a portion of the transition member being openly exposed within the compartment of the container, at least a portion of the transition member having a second diameter that is smaller than the first diameter, the foam contact and transition member being connected together so that an electrical signal can pass therethrough.

2. The foam sensor system as recited in claim 1, wherein the second diameter is equal to or less than ⅓ of the size of the first diameter.

3. The foam sensor system as recited in claim 1, wherein the first diameter is larger than 3 mm and the second diameter is smaller than 1 mm.

4. The foam sensor system as recited in claim 1, wherein the transition member can be bent over an angle of at least 180° without plastic deformation.

5. The foam sensor system as recited in claim 1, wherein the transition member is comprised of a nickel-titanium alloy or a copper-aluminum-nickel alloy.

6. The foam sensor system as recited in claim 1, wherein the transition member has an exposed length in a range between 2 cm and 15 cm.

7. The foam sensor system as recited in claim 1, further comprising a ground assembly mounted on the container and comprising a ground contact disposed within the compartment of the container, the ground assembly being configured so that an electrical potential can be applied between the foam contact and the ground contact.

8. The foam sensor system as recited in claim 1, wherein the container comprises a flexible bag comprised of a polymeric material.

9. The foam sensor system as recited in claim 1, wherein the foam contact and the transition member are comprised of different materials.

10. The foam sensor system as recited in claim 1, wherein the base comprises:
    an elongated body having a first end and an opposing second end; and
    an annular barb encircling and radially outwardly projecting from the body.

11. The foam sensor system as recited in claim 1, further comprising an electrical wire coupled to the base.

12. The foam sensor system as recited in claim 1, further comprising:
    a housing secured to the container and comprising a stem with a flange radially outwardly projecting therefrom, the stem bounding an opening; and
    the base being at least partially disposed within the opening of the stem.

13. The foam sensor system as recited in claim 12, further comprising at least a portion of the transition member being disposed within a portion of the opening of the housing.

14. The foam sensor system as recited in claim 1, further comprising:
    a fluid disposed within the compartment of the container and having a top surface;
    a gas filled gap being formed between the top surface of the fluid and an upper end of the container;
    a ground contact being in contact with the fluid within the compartment;
    the foam contact being disposed within the gap within the container so as to be spaced apart from the fluid; and
    an electrical potential being applied between the foam contact and the ground contact.

15. The foam sensor system as recited in claim 14, further comprising:
    means for mixing the fluid within the compartment of the container;
    the fluid comprising a live culture of cells or microorganisms; and
    a CPU electrically coupled with the foam contact and the ground contact, the CPU being programed to dispense a quantity of an anti-foaming agent into the compartment of the container when an electrical signal passes between the foam contact and the ground contact within the compartment of the container.

16. A method for controlling foam, the method comprising:
    sparging a gas into a fluid located within the compartment of the container of the foam sensor system recited in claim 1, the sparging gas producing a foam on a top surface of the fluid within a head space at an upper end of the container;
    applying an electrical potential between the foam contact located within the head space at a location away from the fluid and a ground contact that is at least partially disposed within the fluid; and
    automatically dispensing an anti-foaming agent into the compartment of the container when the foam produced on the top surface of the fluid touches the foam contact so that an electrical signal is passed between the foam contact and the ground contact.

17. The method as recited in claim 16, wherein the fluid comprises a live culture of cells or microorganisms.

18. The method as recited in claim 16, further comprising sensing the electrical signal and only automatically dispensing the anti-foaming agent when the electrical signal exceeds a predetermined value.

* * * * *